United States Patent [19]

Meyer et al.

[11] 3,951,993

[45] Apr. 20, 1976

[54] 2-AMINO-4,5-DIHYDROPYRIDINE DERIVATIVES AND PROCESS FOR THEIR PREPARATION

[75] Inventors: Horst Meyer, Wuppertal; Friedrich Bossert, Wuppertal-Elberfeld; Wulf Vater, Opladen; Kurt Stoepel, Wuppertal, all of Germany

[73] Assignee: Bayer Aktiengesellschaft, Germany

[22] Filed: Mar. 22, 1974

[21] Appl. No.: 453,863

Related U.S. Application Data

[62] Division of Ser. No. 336,481, Feb. 28, 1973, Pat. No. 3,876,646.

[30] Foreign Application Priority Data

Mar. 6, 1972 Germany............................ 2210659

[52] U.S. Cl...................... 260/294.8 G; 260/283 S;
260/287 R; 260/294.8 D; 260/294.8 F;
260/294.9; 260/295.5 R
[51] Int. Cl.².................................... C07D 213/32
[58] Field of Search............. 260/294.8 D, 294.8 G,
260/295.5 R, 294.8 F, 249.9, 283 S, 287 R

[56] References Cited
UNITED STATES PATENTS
3,876,646    4/1975    Meyer et al. ................. 260/294.8 F OTHER PUBLICATIONS
Klingsberg, Pyridine and Its Derivatives, Part Three, pp. 179 and 181, Interscience Publishers Inc. (1962).
Gewald, Chem. Ber. Vol. 101, pp. 383–390, (1968).
Chemical Abstracts, Vol. 79, Abst. No. 146402k, (1973).

*Primary Examiner*—John D. Randolph

[57] ABSTRACT

2-Amino-4,5-dihydropyridines-3,5-dicarboxylates substituted by lower alkoxy or lower alkylthio in the 6-position and optionally substituted in the 4-position by lower alkyl, phenyl, substituted phenyl or a heterocyclic group are antihypertensive agents and coronary vessel dilators. The compounds, of which 2-amino-4-(3-nitrophenyl)-6-ethoxy-4,5-dihydropyridine-3,5-dicarboxylic acid diethyl ester is a representative embodiment, are prepared through condensation of an aldehyde and a 3-aminoacrylate bearing an alkoxy or alkylthio group in the 3-position.

34 Claims, No Drawings

2-AMINO-4,5-DIHYDROPYRIDINE DERIVATIVES AND PROCESS FOR THEIR PREPARATION

This is a division of application Ser. No. 336,481, filed Feb. 28, 1973, now U.S. Pat. No. 3,876,646, granted Apr. 8, 1975.

DETAILED DESCRIPTION

The present invention pertains to 2-amino-4,5-dihydropyridine derivatives, to processes for their production and use and to pharmaceutical compositions containing such compounds and useful as antihypertensive agents and coronary vessel dilators.

In particular, the present invention pertains to compounds of the formula:

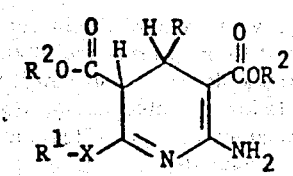

wherein

R is hydrogen; lower alkyl; lower alkenyl; lower alkynyl; phenyl; substituted phenyl in which the substituents are one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio or phenyl; naphthyl; or a heterocyclic ring selected from the group consisting of quinolyl, isoquinolyl, pyridyl, thenyl, furyl and pyrryl, said heterocyclic ring being unsubstituted or substituted by one or two members selected from the group consisting of lower alkyl, lower alkoxy and halogeno;

each of $R^1$ and $R^2$, taken independently of the other, is lower alkyl, lower alkenyl or lower alkynyl; and X is oxygen or sulfur.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

The term lower alkoxy denotes a straight or branched hydrocarbon chain bound to the remainder of the molecule through an ethereal oxygen atom as, for example, methoxy, ethoxy, propoxy, isopropoxy, butoxy, isobutoxy, pentoxy and hexoxy.

The term lower alkylthio denotes a branched or straight hydrocarbon chain bound to the remainder of the molecule through a divalent sulfur as, for example, methylthio, ethylthio, propylthio, isopropylthio, butylthio, and the like.

The term halogen denotes the substituents fluoro, chloro, bromo and iodo.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting an aldehyde of the formula:

RCHO wherein R is as herein defined, with a 3-alkoxy- or 3-alkylthio-3-aminoacrylate of the formula:

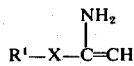

in which $R^1$, $R^2$ and X are as herein defined. The condensation proceeds smoothly in good yields simply by heating the two components, generally in the presence of an inert organic solvent such as methanol, ethanol, propanol and similar alkanols, ethers such as dioxane and diethyl ether, glacial acetic acid, pyridine, dimethyformamide, dimethylsulfoxide, acetonitrile, and the like. The reaction is conducted at temperatures of from 20° to 250°C, conveniently at the boiling point of the solvent, and while elevated pressure may be utilized, normal atmospheric pressure is generally satisfactory. The acrylate reactant is generally employed in about a two-fold molar excess.

It is rather surprising that the above described condensation produces the desired compounds in such good yields and with such high purity since it is known that an aldehyde condenses with an amino crotonic acid ester to yield a 1,4-dihydropyridine (Cook et al., J. Chem. Soc. 1943, 413). This is particularly true since it would be expected that the 3-aminoacrylate reactant, which can be considered as an imino or thioimino ether, would yield the 2,6-dialkoxy-1,4-dihydropyridine derivative, Cope, J.A.C.S., 67 1017 (1945).

Many of the aldehydes utilized as one of the reactants are known to the art and the others can either be generated in situ as herein described or prepared according to methods well known to the art, see for example Org. Reactions VIII, 218 et seq. (1954). Typical of this reactants are reactant following compounds:

formaldehyde,
acetaldehyde,
propionaldehyde,
isobutyraldehyde,
cyclopentaldehyde,
cyclohexanaldehyde,
acrolein,
cyclohex-3-enaldehyde,
benzaldehyde,
2-, 3- and 4-methylbenzaldehyde,
2-, 3- and 4-methoxybenzaldehyde,
3,4 and 5-trimethoxybenzaldehyde,
2-isopropoxybenzaldehyde,
2-, 3- and 4-chlorobenzaldehyde,
2-, 3- and 4-bromobenzaldehyde, 2-, 3- and 4-fluorobenzaldehyde,
2,4- and 2,6-dichlorobenzaldehyde,
2,4- and 2,3-dimethylbenzaldehyde,
2-, 3- and 4-nitrobenzaldehyde,
2,6- and 3,5-dinitrobenzaldehyde,
2-nitro-6-bromobenzaldehyde,
2-nitro-3-methoxy-6-chlorobenzaldehyde,
2-nitro-4-chlorobenzaldehyde,
2-nitro-4-methoxybenzaldehyde,
2-, 3- and 4-trifluoromethylbenzaldehyde,
2-carbethoxybenzaldehyde,
3-carbomethoxybenzaldehyde,
4-carbobutoxybenzaldehyde,
3-nitro-4-carbethoxybenzaldehyde-4-carboxylic acid ethyl ester,
α,β- and γ-pyridinaldehyde,
6-methylpyridin-2-aldehyde,
pyrimidin-5-aldehyde,
4,6-dimethoxypyrimidin-5-aldehyde,
2-, 3- and 4-cyanobenzaldehyde,
2-methylmercaptobenzaldehyde,
4-methylmercaptobenzaldehyde,
2-methylsulphonylbenzaldehyde,
1- and 2-naphthaldehyde,
5-bromo-1-naphthaldehyde,
2-ethoxy-1-naphthaldehyde,
4-methyl-1-naphthaldehyde,
quinolin-2-, 3-, 4-, 5-, 6-, 7- and 8-aldehyde,
isoquinolin-1,3,4-aldehyde,
furan-2-aldehyde,
thiophen-2-aldehyde and
pyrrol-2-aldehyde.

The 3-substituted 3-aminoacrylate reactants are similarly known or can be readily produced according to known methods, see for example Cope, J.A.C.S., 67, 1017 (1945). Typical of these reactants are the following:

3-amino-3-methoxyacrylic acid methyl ester,
3-amino-3-methoxyacrylic acid ethyl ester,
3-amino-3-methoxyacrylic acid propyl ester,
3-amino-3-ethoxyacrylic acid methyl ester,
3-amino-3-ethoxyacrylic acid ethyl ester,
3-amino-3-ethoxyacrylic acid isopropyl ester,
3-amino-3-propoxyacrylic acid ethyl ester,
3-amino-3-isopropoxyacrylic acid ethyl ester,
3-amino-3-isopropoxyacrylic acid n-propyl ester,
3-amino-3-ethoxyacrylic acid cyclohexyl ester,
3-amino-3-ethoxyacrylic acid β-methoxyethyl ester,
3-amino-3-methylmercaptoacrylic acid ethyl ester,
3-amino-3-ethylmercaptoacrylic acid ethyl ester, and
3-amino-3-ethylmercaptoacrylic acid methyl ester.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example a coronary vessel dilation effect can be observed by measuring the increase in oxygen saturation in the coronary sinus in the narcotized, heart catheterized dog, as shown in the following table showing the doses at which a clearly detectable rise is observed:

| Compound | I.V. Dose (mg/kg) |
| --- | --- |
| 2-amino-4-methyl-6-ethoxy-4,5-dihydropyridine-3,5-dicarboxylic acid diethyl ester | 2 to 5 |
| 2-amino-4-(2-nitrophenyl)-6-ethoxy-4,5-dihydropyridine-3,5-dicarboxylic acid diethyl ester | 3 to 5 |
| 2-amino-4-(3-nitrophenyl)-6-ethoxy-4,5-dihydropyridine-3,5-dicarboxylic acid diethyl ester | 2 |

The hypotensive activity of the present compounds can be observed by measuring the blood pressure of hypertensive rats following administration of the compounds. The following table demonstrates the dose which results in at least a 15 mm Hg reduction in blood pressure of such animals:

| Compound | I.V. Dose (mg/kg) |
| --- | --- |
| 2-amino-4-(2-nitrophenyl)-6-ethoxy-4,5-dihydropyridine-3,5-dicarboxylic acid diethyl ester | 10.0 |
| 2-amino-4-(3-nitrophenyl)-6-ethoxy-4,5-dihydropyridine-3,5-dicarboxylic acid diethyl ester | 1.0 |
| 2-amino-4-(4-chlorophenyl)-6-ethoxy-4,5-dihydropyridine-3,5-dicarboxylic acid diethyl ester | 3.1 |

The toxicity of the compounds is also favorably low.

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascularspasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5%, of at least one 2-amino-4,5-dihydropyridine as herein defined in combination with a pharmaceutical carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 5 mg/kg, when administered parenterally and from about 1 to about 100 mg/kg, preferably 5 to 50 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solution, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax, or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of the invention since the subject matter regarded as the invention is set forth in the appended claims.

Example 1

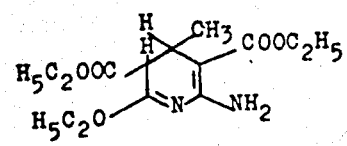

Boiling a solution of 2.4 g of acetaldehyde and 19 g of 3-amino-3-ethoxyacrylic acid ethyl ester in 30 ml of alcohol for 8 hours yields 2-amino-4-methyl-6-ethoxy-4,5-dihydropyridine-3,5-dicarboxylic acid diethyl ester of melting point 64°C (petroleum ether/ethyl acetate).
Yield: 57% of theory.

Example 2

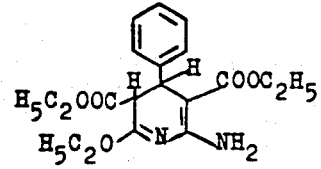

Upon boiling a solution of 5.3 g of benzaldehyde and 15.9 g of 3-amino-3-ethoxyacrylic acid ethyl ester in 30 ml of alcohol for 12 hours, 2-amino-4-phenyl-6-ethoxy-4,5-dihydropyridine-3,5-dicarboxylic acid diethyl ester of melting point 119°C (isopropanol) is obtained.

Yield: 64% of theory.

Example 3

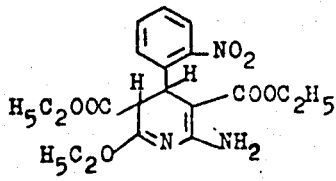

Heating a solution of 7.6 g of 2-nitrobenzaldehyde and 15.9 of 3-amino-3-ethoxyacrylic acid ethyl ester in 50 ml of alcohol for 8 hours yields 2-amino-4-(2-nitrophenyl)-6-ethoxy-4,5-dihydropyridine-3,5-dicarboxylic acid ethyl ester of melting point 133°–4°C (isopropanol).

Yield: 59% of theory.

Example 4

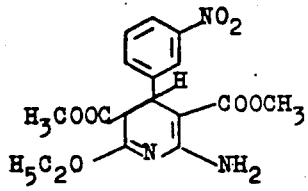

Upon boiling a solution of 7.6 g of 3-nitrobenzaldehyde and 14.5 g of 3-amino-3-ethoxyacrylic acid methyl ester in 40 ml of alcohol for 6 hours, 2-amino-4-(3-nitrophenyl)-6-ethoxy-4,5-dihydropyridine-3,5-dicarboxylic acid dimethyl ester of melting point 163°C (isopropanol) is obtained.

Yield: 71% of theory.

Example 5

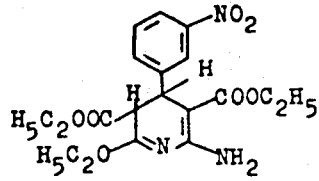

Upon heating a solution of 7.6 g of 3-nitrobenzaldehyde and 15.9 g of 3-amino-3-ethoxyacrylic acid ethyl ester in 50 ml of isopropanol for 6 hours, 2-amino-4-(3-nitrophenyl)-6-ethoxy-4,5-dihydropyridine-3,5-dicarboxylic acid diethyl ester of melting point 129° (isopropanol) is obtained.

Yield: 68% of theory.

Example 6

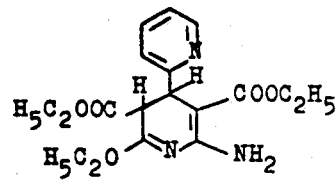

Boiling a solution of 5.4 g of pyridin-2-aldehyde and 15.9 g of 3-amino-3-ethoxyacrylic acid ethyl ester in 50 ml of alcohol for 8 hours yields 2-amino-4-(α-pyridyl)-6-ethoxy-4,5-dihydropyridine-3,5-dicarboxylic acid diethyl ester of melting point 98°C (petroleum ether/ether).

Yield: 55% of theory.

Example 7

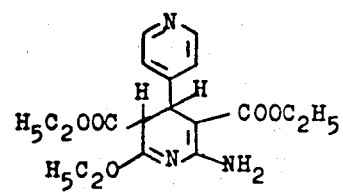

Upon heating a solution of 5.4 g of pyridin-4-aldehyde and 15.9 g of 3-amino-3-ethoxyacrylic acid ethyl ester in 50 ml of alcohol for 12 hours, 2-amino-4-(γ-pyridyl)-6-ethoxy-4,5-dihydropyridine-3,5-dicarboxylic acid diethyl ester of melting point 111°C (petroleum ether/ethyl acetate) is obtained.

Yield: 72% of theory.

Example 8

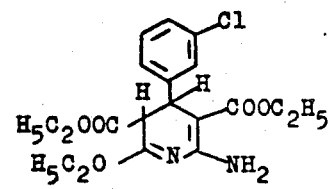

Upon boiling a solution of 7.1 g of 3-chlorobenzaldehyde and 15.9 g of 3-amino-3-ethoxyacrylic acid ethyl ester in 40 ml of isopropanol for 8 hours, 2-amino-4-(3-chlorophenyl)-6-ethoxy-4,5-dihydropyridine-3,5-

Example 9

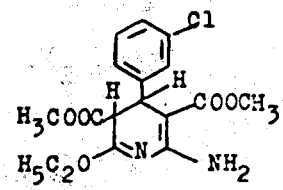

Upon heating a solution of 7.1 g of 3-chlorobenzaldehyde and 14.5 g of 3-amino-3-ethoxyacrylic acid methyl ester in 50 ml of isopropanol for 6 hours, 2-amino-4-(3-chlorophenyl)-6-ethoxy-4,5-dihydropyridine-3,5-dicarboxylic acid dimethyl ester of melting point 158°C (isopropanol) is obtained.

Yield: 78% of theory.

Example 10

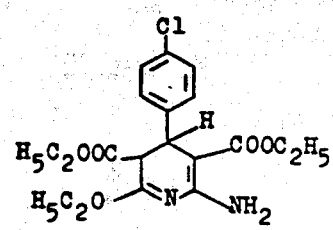

Boiling a solution of 7.1 g of 4-chlorobenzaldehyde and 15.9 g of 3-amino-3-ethoxyacrylic acid ethyl ester in 50 ml of alcohol for 8 hours yields 2-amino-4-(4-chlorophenyl)-6-ethoxy-4,5-dihydropyridine-3,5-dicarboxylic acid diethyl ester of melting point 130°–132°C (ethyl acetate/petroleum ether).

Yield: 56% of theory.

Example 11

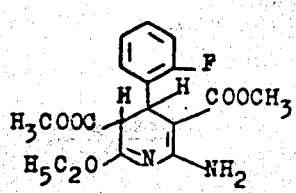

Heating a solution of 6.3 g of 2-fluorobenzaldehyde and 14.5 g of 3-amino-3-ethoxyacrylic acid methyl ester in 50 ml isopropanol for 8 hours yields 2-amino-4-(2-fluorophenyl)-6-ethoxy-4,5-dihydropyridine-3,5-dicarboxylic acid dimethyl ester of melting point 180°C (isopropanol).

Yield: 59% of theory.

Example 12

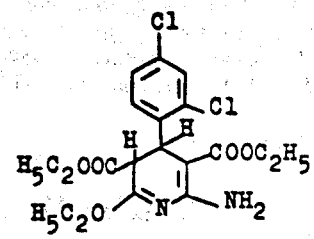

Upon boiling a solution of 8.8 g of 2,4-dichlorobenzaldehyde and 15.9 g of 3-amino-3-ethoxyacrylic acid ethyl ester in 50 ml of alcohol for 6 hours, 2-amino-4-(2,4-dichlorophenyl)-6-ethoxy-4,5-dihydropyridine-3,5-dicarboxylic acid diethyl ester of melting point 98°C (ethyl acetate/petroleum ether) is obtained.

Yield: 68% of theory.

Example 13

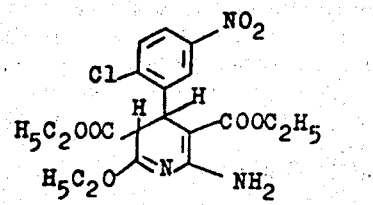

Upon heating a solution of 9.3 g of 3-nitro-6-chlorobenzaldehyde and 15.9 g of 3-amino-3-ethoxyacrylic acid ethyl ester in 50 ml of isopropanol for 6 hours, 2-amino-4-(3-nitro-6-chlorophenyl)-6-ethoxy-4,5-dihydropyridine-3,5-dicarboxylic acid diethyl ester of melting point 136°–37°C (isopropanol) is obtained.

Yield: 65% of theory.

Example 14

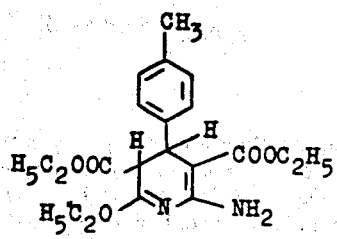

Upon heating a solution of 6 g of 4-methylbenzaldehyde and 15.9 g of 3-amino-3-ethoxyacrylic acid ethyl ester in 50 ml of alcohol for 6 hours, 2-amino-4-(4-methylphenyl)-6-ethoxy-4,5-dihydropyridine-3,5-dicarboxylic acid diethyl ester of melting point 119°C (ethyl acetate/petroleum ether) is obtained.

Yield: 47% of theory.

Example 15

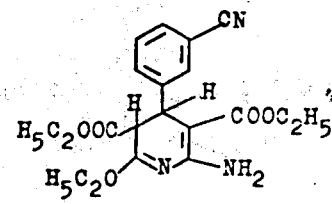

Boiling a solution of 6.5 g of 3-cyanobenzaldehyde and 15.9 g of 3-amino-3-ethoxyacrylic acid ethyl ester in 50 ml of ethanol for 8 hours yields 2-amino-4-(3-cyanophenyl)-6-ethoxy-4,5-dihydropyridine-3,5-dicarboxylic acid diethyl ester of melting point 159°C (isopropanol).

Yield: 73% of theory.

Example 16

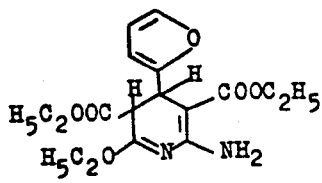

Upon heating a solution of 4.8 g of furan-2-aldehyde and 15.9 g of 3-amino-3-ethoxy-acrylic acid ethyl ester in 50 ml of alcohol for 8 hours, 2-amino-4-(2-furyl)-6-ethoxy-4,5-dihydropyridine-3,5-dicarboxylic acid diethyl ester of melting point 110°C (isopropanol) is obtained.

Yield: 62% of theory.

Example 17

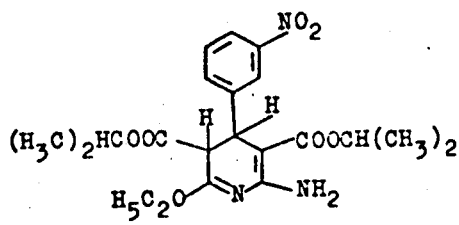

Heating a solution of 6.1 g of 3-nitrobenzaldehyde and 13.9 g of 3-amino-3-ethoxyacrylic acid isopropyl ester in 100 ml of ethanol for 8 hours yields 2-amino-6-ethoxy-4-(3-nitrophenyl)-4,5-dihydropyridine-3,5-dicarboxylic acid diisopropyl ester of melting point 130°C (ether/petroleum ether).

Yield: 45% of theory.

Example 18

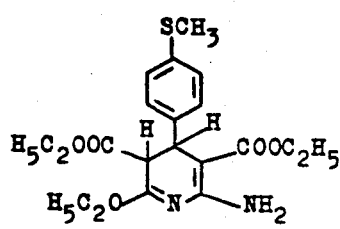

Heating a solution of 7.6 g of 4-methylmercaptobenzaldehyde and 15.9 g of 3-amino-3-ethoxyacrylic acid ethyl ester in 100 ml of ethanol for 8 hours yields 2-amino-6-ethoxy-4-(4-methylmercaptophenyl)-4,5-dihydropyridine-3,5-dicarboxylic acid diethyl ester of melting point 132°C (isopropanol).

Yield: 52% of theory.

Example 19

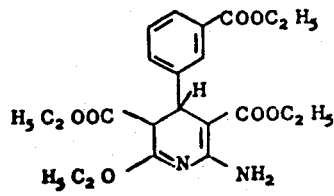

Upon heating of a solution of 8.9 g of 3-carbethoxybenzaldehyde and 15.9 g of 3-amino-4-ethoxyacrylic acid ethyl ester in 50 ml of ethanol for 8 hours, 2-amino-4-(3-carbethoxyphenyl)-6-ethoxy-4,5-dihydropyridine-3,5-dicarboxylic acid diethyl ester of m.p. 87°C (isopropanol) is obtained.

Yield: 56% of theory.

Example 20

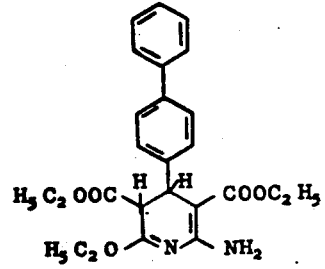

Upon boiling of a solution of 9.1 g of biphenyl-4-aldehyde and 1.5 g of 3-amino-3-ethoxyacrylic acid ethyl ester in 50 ml of ethanol for 8 hours, 2-amino-4-(4-biphenylyl)-6-ethoxy-4,5-dihydropyridine-3,5-dicarboxylic acid diethyl ester of m.p. 145°C (isopropanol) is obtained.

Yield: 48% of theory.

Example 21

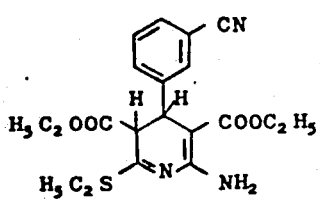

Upon boiling a solution of 6.5 g of 3-cyanobenzaldehyde and 17.5 g of 3-amino-3-ethylmercaptoacrylic acid ethyl ester in 100 ml of ethanol for 5 hours, 2-amino-4-(3-cyanophenyl)-6-ethylmercapto-4,5-dihydropyridine-3,5-dicarboxylic acid diethyl ester of melting point 153°C (isopropanol) is obtained.
Yield: 38% of theory.

Example 22

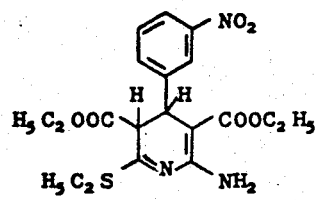

Upon heating a solution of 7.6 g of 3-nitrobenzaldehyde and 17.5 g of 3-amino-3-ethylmercaptoacrylic acid ethyl ester in 100 ml of ethanol for 6 hours, 2-amino-4-(3-nitrophenyl)-6-ethylmercapto-4,5-dihydropyridine-3,5-dicarboxylic acid diethyl ester of melting point 187°C (isopropanol) is obtained.
Yield: 44% of theory.

Example 23

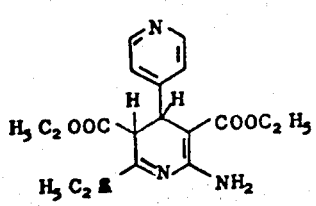

Upon boiling a solution of 5.3 g of pyridine-4-aldehyde and 17.5 g of 3-amino-3-ethylmercaptoacrylic acid ethyl ester in 100 ml of ethanol for 5 hours, 2-amino-4-(4-pyridyl)-6-ethylmercapto-4,5-dihydropyridine-3,5-dicarboxylic acid diethyl ester of melting point 156°C is obtained.
Yield: 47% of theory.

Example 24

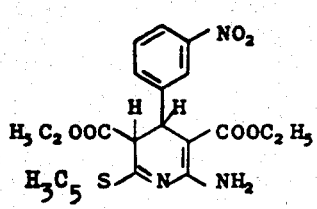

Upon heating a solution of 15.1 g of 3-amino-3-methylmercaptoacrylic acid ethyl ester and 7.6 g of 3-nitrobenzaldehyde in 100 ml of ethanol for 5 hours, 2-amino-4-(3-nitrophenyl)-6-methylmercapto-4,5-dihydropyridine-3,5-dicarboxylic acid diethyl ester of melting point 144°C (isopropanol) is obtained.
Yield: 39% of theory.

Example 25

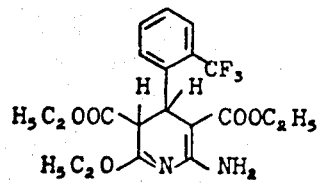

Upon heating of a solution of 8.7 g of 2-trifluoromethylbenzaldehyde and 15.9 g of 3-amino-3-ethoxyacrylic acid ethyl ester in 100 ml ethanol for 8 hours, 2-amino-4-(2-trifluoromethylphenyl)-6-ethoxy-4,5-dihydropyridine-3,5-dicarboxylic acid diethyl ester of m.p. 116°C (ether) is obtained.
Yield: 51% of theory.

What is claimed is:
1. A process for the production of a compound of the formula

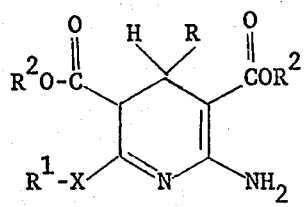

wherein
R is hydrogen; lower alkyl; lower alkenyl; lower alkynyl; phenyl; substituted phenyl in which the substituents are one to three members selected from the group consisting of lower alkyl, lower alkoxy, halogen, nitro, cyano, trifluoromethyl, azido, carbo(lower alkoxy), lower alkylsulfonyl, lower alkylsulfinyl, lower alkylthio or phenyl; naphthyl; or a heterocyclic ring selected from the group consisting of quinolyl, isoquinolyl, pyridyl, thenyl, furyl and pyrryl, said heterocyclic ring being unsubstituted or substituted by one or two members selected from the group consisting of lower alkyl, lower alkoxy and halogeno;
each of $R^1$ and $R^2$, taken independently of the other, is lower alkyl, lower alkenyl or lower alkynyl; and
X is oxygen or sulfur; which comprises reacting an aldehyde of the formula RCHO, wherein R is as above defined, with a 3-alkoxy- or 3-alkylthio-3-aminoacrylate of the formula

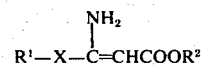

wherein $R^1$, $R^2$ and X are as above defined, there being at least two molar equivalents of said aldehyde per molar equivalent of said acrylate, at a temperature of from 20° C to 250° C and recovering the compound produced.

2. A process according to claim 1 wherein R¹ and R² are lower alkyl.

3. A process according to claim 2 wherein R is quinolyl, isoquinolyl, pyridyl, phenyl, furyl or pyrryl, unsubstituted or substituted by 1 or 2 members selected from the group consisting of lower alkyl, lower alkoxy and halogeno.

4. A process according to claim 2 wherein R is lower alkyl, naphthyl, phenyl or phenyl substituted with from one to three substituents selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio or phenyl.

5. The method of preparing a compound according to claim 1 which comprises treating an aldehyde of the formula RCHO wherein R is as therein defined with a 3-substituted-3-aminoacrylate of the formula

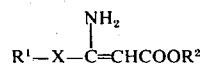

wherein R¹, R² and X are as therein defined in the presence of an inert organic solvent.

6. A process according to claim 1 wherein R is lower alkyl, phenyl, phenyl substituted by lower alkyl, chlorine, fluorine, nitro, cyano, trifluoromethyl, carbo(lower alkoxy), lower alkylthio, phenyl, dichlorine or chlorine and nitro, pyridyl or furyl; R¹ is methyl, ethyl or propyl; and R² is ethyl.

7. A process according to claim 1, wherein the reaction is carried out in the presence of an inert organic solvent.

8. A process according to claim 7 wherein the inert organic solvent is methanol, ethanol, propanol, dioxane, diethyl ether, glacial acetic acid, pyridine, dimethylformamide, dimethylsulfoxide or acetonitrile.

9. A process according to claim 7 wherein the reaction is carried out at the boiling point of the solvent.

10. A process according to claim 1 for the production of 2-amino-4-methyl-6-ethoxy-4,5-dihydropyridine-3,5-dicarboxylic acid diethyl ester which comprises reacting acetaldehydr and 3-amino-3-ethoxyacrylic acid ethyl ester in alcohol at the boiling point of the alcohol and recovering the compound produced.

11. A process according to claim 1 for the production of 2-amino-4-phenyl-6-ethoxy-4,5-dihydropyridine-3,5-dicarboxylic acid diethyl ester which comprises reacting benzaldehyde and 3-amino-3-ethoxyacrylic acid ethyl ester in alcohol at the boiling point of the alcohol and recovering the compound produced.

12. A process according to claim 1 for the production of 2-amino-4-(2-nitrophenyl)-6-ethoxy-4,5-dihydropyridine-3,5-dicarboxylic acid ethyl ester which comprises heating 2-nitrobenzaldehyde and 3-amino-3-ethoxyacrylic acid ethyl ester in alcohol and recovering the compound produced.

13. A process according to claim 1 for the production of 2-amino-4-(3-nitrophenyl)-6-ethoxy-4,5-dihydropyridine-3,5-dicarboxylic acid dimethyl ester which comprises reacting 3-nitrobenzaldehyde and 3-amino-3-ethoxyacrylic acid methyl ester in alcohol at the boiling point of alcohol and recovering the compound produced.

14. A process according to claim 1 for the production of 2-amino-4-(3-nitrophenyl)-6-ethoxy-4',5-dihydropyridine-3,5-dicarboxylic acid diethyl ester which comprises heating 3-nitrobenzaldehyde and 3-amino-3-ethoxyacrylic acid ethyl ester in isopropanol and recovering the compound produced.

15. A process according to claim 1 for the production of 2-amino-4-(α-pyridyl)-6-ethoxy-4,5-dihydropyridine-3,5-dicarboxylic acid diethyl ester which comprises reacting pyridin-2-aldehyde and 3-amino-3-ethoxyacrylic acid ethyl ester in alcohol at the boiling point of the alcohol and recovering the compound produced.

16. A process according to claim 1 for the production of 2-amino-4-(γ-pyridyl)-6-ethoxy-4,5-dihydropyridine-3,5-dicarboxylic acid diethyl ester which comprises heating pyridin-4-aldehyde and 3-amino-3-ethoxyacrylic acid ethyl ester in alcohol and recovering the compound produced.

17. A process according to claim 1 for the production of 2-amino-4-(3-chlorophenyl-6-ethoxy-4,5-dihydropyridine-3,5-dicarboxylic acid diethyl ester which comprises reacting 3-chlorobenzaldehyde and 3-amino-3-ethoxyacrylic acid ethyl ester in isopropanol at the boiling point of isopropanol and recovering the compound produced.

18. A process according to claim 1 for the production of 2-amino-4-(3-chlorophenyl)-6-ethoxy-4,5-dihydropyridine-3,5-dicarboxylic acid dimethyl ester which comprises heating 3-chlorobenzaldehyde and 3-amino-3-ethoxyacrylic acid methyl ester in isopropanol and recovering the compound produced.

19. A process according to claim 1 for the production of 2-amino-4-(4-chlorophenyl)-6-ethoxy-4,5-dihydropyridine-3,5-dicarboxylic acid diethyl ester which comprises reacting 4-chlorobenzaldehyde and 3-amino-3-ethoxyacrylic acid ethyl ester in alcohol at the boiling point of alcohol and recovering the compound produced.

20. A process according to claim 1 for the production of 2-amino-4-(2-fluorophenyl)-6-ethoxy-4,5-dihydropyridine-3,5-dicarboxylic acid dimethyl ester which comprises heating 2-fluorobenzaldehyde and 3-amino-3-ethoxyacrylic acid methyl ester in isopropanol and recovering the compound produced.

21. A process according to claim 1 for the production of 2-amino-4-(2,4-dichlorophenyl)-6-ethoxy-4,5-dihydropyridine-3,5-dicarboxylic acid diethyl ester which comprises reacting 2,4-dichlorobenzaldehyde and 3-amino-3-ethoxyacrylic acid ethyl ester in alcohol at the boiling point of alcohol and recovering the compound produced.

22. A process according to claim 1 for the production of 2-amino-4-(3-nitro-6-chlorophenyl)-6-ethoxy-4,5-dihydropyridine-3,5-dicarboxylic acid diethyl ester which comprises heating 3-nitro-6-chlorobenzaldehyde and 3-amino-3-ethoxyacrylic acid ethyl ester in isopropanol and recovering the compound produced.

23. A process according to claim 1 for the production of 2-amino-4-(4-methylphenyl)-6-ethoxy-4,5-dihydropyridine-3,5-dicarboxylic acid diethyl ester which comprises heating 4-methylbenzaldehyde and 3-amino-3-ethoxyacrylic acid ethyl ester in alcohol and recovering the compound produced.

24. A process according to claim 1 for the production of 2-amino-4-(3-cyanophenyl)-6-ethoxy-4,5-dihydropyridine-3,5-dicarboxylic acid diethyl ester which comprises reacting 3-cyanobenzaldehyde and 3-amino-3-ethoxyacrylic acid ethyl ester in ethanol at the boiling point of ethanol and recovering the compound produced.

25. A process according to claim 1 for the production of 2-amino-4-(2-furyl)-6-ethoxy-4,5-dihydropyridine-3,5-dicarboxylic acid diethyl ester which comprises heating furan-2-aldehyde and 3-amino-3-ethoxyacrylic acid ethyl ester in alcohol and recovering the compound produced.

26. A process according to claim 1 for the production of 2-amino-6-ethoxy-4-(3-nitrophenyl)-4,5-dihydropyridine-3,5-dicarboxylic acid diisopropyl ester which comprises heating 3-nitrobenzaldehyde and 3-amino-3-ethoxyacrylic acid isopropyl ester in ethanol and recovering the compound produced.

27. A process according to claim 1 for the production of 2-amino-6-ethoxy-4-(4-methylmercaptophenyl)-4,5-dihydropyridine-3,5-dicarboxylic acid diethyl ester which comprises heating 4-methylmercaptobenzaldehyde and 3-amino-3-ethoxyacrylic acid ethyl ester in ethanol and recovering the compound produced.

28. A process according to claim 1 for the production of 2-amino-4-(3-carbethoxyphenyl)-6-ethoxy-4,5-dihydropyridine-3,5-dicarboxylic acid diethyl ester which comprises heating 3-carbethoxybenzaldehyde and 3-amino-4-ethoxyacrylic acid ethyl ester in ethanol and recovering the compound produced.

29. A process according to claim 1 for the production of 2-amino-4-(4-biphenylyl)-6-ethoxy-4,5-dihydropyridine-3,5-dicarboxylic acid diethyl ester which comprises reacting biphenyl-4-aldehyde and 3-amino-3-ethoxyacrylic acid ethyl ester in ethanol at the boiling point of ethanol and recovering the compound produced.

30. A process according to claim 1 for the production of 2-amino-4-(3-cyanophenyl)-6-ethylmercapto-4,5-dihydropyridine-3,5-dicarboxylic acid diethyl ester which comprises reacting 3-cyanobenzaldehyde and 3-amino-3-ethylmercaptoacrylic acid ethyl ester in ethanol at the boiling point of ethanol and recovering the compound produced.

31. A process according to claim 1 for the production of 2-amino-4-(3-nitrophenyl)-6-ethylmercapto-4,5-dihydropyridine-3,5-dicarboxylic acid diethyl ester which comprises heating 3-nitrobenzaldehyde and 3-amino-3-ethylmercaptoacrylic acid ethyl ester in ethanol and recovering the compound produced.

32. A process according to claim 1 for the production of 2-amino-4-(4-pyridyl)-6-ethylmercapto-4,5-dihydropyridine-3,5-dicarboxylic acid diethyl ester which comprises reacting pyridine-4-aldehyde and 3-amino-3-ethylmercaptoacrylic acid ethyl ester in ethanol at the boiling point of ethanol and recovering the compound produced.

33. A process according to claim 1 for the production of 2-amino-4-(3-nitrophenyl)-6-methylmercapto-4,5-dihydropyridine-3,5-dicarboxylic acid diethyl ester which comprises heating 3-amino-3-methylmercaptoacrylic acid ethyl ester and 3-nitrobenzaldehyde in ethanol and recovering the compound produced.

34. A process according to claim 1 for the production of 2-amino-4-(2-trifluoromethylphenyl)-6-ethoxy-4,5-dihydropyridine-3,5-dicarboxylic acid diethyl ester which comprises heating 2-trifluoromethylbenzaldehyde and 3-amino-3-ethoxyacrylic acid ethyl ester in ethanol and recovering the compound produced.

\* \* \* \* \*